US00PP28744P3

(12) United States Plant Patent
O'Connell

(10) Patent No.: US PP28,744 P3
(45) Date of Patent: Dec. 5, 2017

(54) ***ECHEVERIA* PLANT NAMED 'ANDROMEDA'**

(50) Latin Name: ***Echeveria* hybrid**
Varietal Denomination: Andromeda

(71) Applicant: Renee O'Connell, Escondido, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 50 days.

(21) Appl. No.: 14/756,716

(22) Filed: Oct. 1, 2015

(65) Prior Publication Data

US 2017/0099763 P1 Apr. 6, 2017

(51) Int. Cl.
*A01H 5/02* (2006.01)

(52) U.S. Cl.
USPC ..... Plt./373

(58) Field of Classification Search
USPC ..... Plt./373, 263.1
See application file for complete search history.

*Primary Examiner* — Keith Robinson
(74) *Attorney, Agent, or Firm* — Cassandra Bright

(57) ABSTRACT

A new and distinct *Echeveria* cultivar named 'Andromeda' is disclosed, characterized by large rosettes comprised of an abundance of ruffled, silvery blue-violet leaves, margined with pink. Further, the new cultivar 'Andromeda' produces complex inflorescences, comprised of 3-5 cincinni, composed of 17-21 flowers each, resulting in profuse flowering. 2.4 cm long flowers produced are exceptionally large for the genus. Robust growth, enhancing production intervals in the commercial nursery. Plants are landscape tolerant in temperate areas, and grow quickly to over 20" in diameter. The new variety is an *Echeveria*, part of the Crassulaceae complex that includes *Aeonium, Crassula, Graptopetalum, Pachyphytum, Sedum* and others. *Echeveria* is a popular genus, typically produced as container plants for the patio or as landscape plants, as a variety of ornamental purposes.

3 Drawing Sheets

Latin name of the genus and species: *Echeveria* hybrid.
Variety denomination: 'ANDROMEDA'.

BACKGROUND OF THE INVENTION

The new cultivar, *Echeveria* 'Andromeda', is the product of a planned breeding program. The new variety originated from a cross pollination of the proprietary, unpatented, seed parent, *Echeveria* 'AFT 17' with the pollen parent, an unpatented, proprietary variety of *Echeveria* referred to as '0P1'. The cross pollination was made during May 2011 in Vista, Calif., at a commercial greenhouse. The new cultivar 'Andromeda' was discovered by the inventor, Renee O'Connell, in March 2012, in Vista, Calif., at a commercial greenhouse.

Asexual reproduction of the new cultivar 'Andromeda' was first performed in Vista, Calif., at a commercial greenhouse, by terminal vegetative cuttings in 2012. *Echeveria* 'Andromeda' has since produced multiple generations and has shown that the unique features of this cultivar are stable and reproduced true to type.

SUMMARY OF THE INVENTION

The cultivar 'Andromeda' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ANDROMEDA'. These characteristics in combination distinguish 'ANDROMEDA' as a new and distinct *Echeveria* cultivar:

1. *Echeveria* 'Andromeda' displays large rosettes, comprised of an abundance of silvery blue violet, somewhat undulate, crispate leaves that are margined with pink.
2. *Echeveria* 'Andromeda' produces complex inflorescences, composed of 3-5 cincinni, each with 17-21 flowers, resulting in a profusely flowering *Echeveria.*
3. *Echeveria* 'Andromeda' produces 2.4 cm long flowers, which are exceptionally large for the *Echeveria* genus
4. The quantity of flowers, in combination with the size of the flowers displayed by *Echeveria* 'Andromeda', creates a spectacular floral display.
5. *Echeveria* 'Andromeda' is landscape tolerant in temperate areas, and quickly grows to over 20" in diameter, adding a colorful accent to the landscape or garden.
6. *Echeveria* 'Andromeda' produces robust growth, thereby reducing production intervals in the commercial nursery.

PARENTAL COMPARISON

Plants of the new cultivar 'Andromeda' are similar to the seed parent *Echeveria* 'AFT 17' in most horticultural characteristics. However, plants of the new cultivar 'Andromeda' form rosettes that grow to 20" or more in diameter, much larger as compared with the rosettes of the seed parent *Echeveria* 'AFT 17'. In addition, the new cultivar 'Andromeda' exhibits a more complex inflorescence with 3-5 cincinni or more of 17-20 flowers each, resulting in a spectacular floral display, not exhibited by the seed parent *Echeveria* 'AFT 17'. Plants of the new cultivar 'Andromeda' have much larger flowers, with corollas over 20 mm in length, as compared with the smaller flowers of the seed parent *Echeveria* 'AFT 17'. The new cultivar 'Andromeda' grows moderately fast, enhancing propagation and production times, as compared with the slower growth of the seed parent *Echeveria* 'AFT 17'.

Plants of the new cultivar 'Andromeda' are similar to the pollen parent, the unpatented variety *Echeveria* '0P1', in most horticultural characteristics. However, the new cultivar 'Andromeda' displays larger flowers than those borne by the pollen parent '0P1'. In addition, the new cultivar 'Andromeda' produces complex inflorescences, with 3-5 cincinni composed of 17-20 flowers each, creating a spectacular floral display, not displayed by the pollen parent *Echeveria* '0P1'.

COMMERCIAL COMPARISON

The new cultivar 'Andromeda' can be compared to the unpatented, unnamed *Echeveria subrigida.* Plants of the *Echeveria subrigida* are similar to plants of the new cultivar 'Andromeda' in most horticultural characteristics. However, the new cultivar 'Andromeda' displays a more concentric rosette, enabling shipping without damage, whereas *Echeveria subrigida* produces rosettes of longer leaves that extend over the edge of the pot and are more prone to breakage during shipping. In addition, the new cultivar 'Andromeda' produces complex inflorescences of 3-5 cincinni, comprised of 17-20 large flowers each, resulting in a spectacular floral display, not exhibited by *Echeveria subrigida.*

The new cultivar 'Andromeda' can be compared to the unpatented commercial variety *Echeveria* 'Strawberry Hearts'. Plants of the *Echeveria* 'Strawberry Hearts' are similar to plants of the new cultivar 'Andromeda' in most horticultural characteristics. However, the new cultivar 'Andromeda' form large, low-growing rosettes of 20" in diameter, as compared to *Echeveria* 'Strawberry Hearts', which produces rosettes that tend to grow upward, rather than laterally, and eventually becoming top-heavy rosettes atop tall stems. Plants of the cultivar 'Andromeda' produce complex inflorescences of 3-5 cincini , comprised of 17-20 larger flowers each, resulting in spectacular floral displays, not exhibited by *Echeveria* 'Strawberry Hearts'.

BRIEF DESCRIPTION OF THE PHOTOGRAPHS

The accompanying photographs in FIG. 1 through FIG. 3 illustrate in full color typical plants of 'ANDROMEDA' grown in a greenhouse in Vista, Calif. Age of the plant in each photo is approximately 6 months. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The following photographs depict plants grown under natural light conditions of 2500-4000 foot-candles. Temperatures ranged from −1° C. to 29° C. night and day. No artificial light, photoperiodic treatments or chemical treatments were given to the plants.

DETAILED BOTANICAL DESCRIPTION

Figure 1:
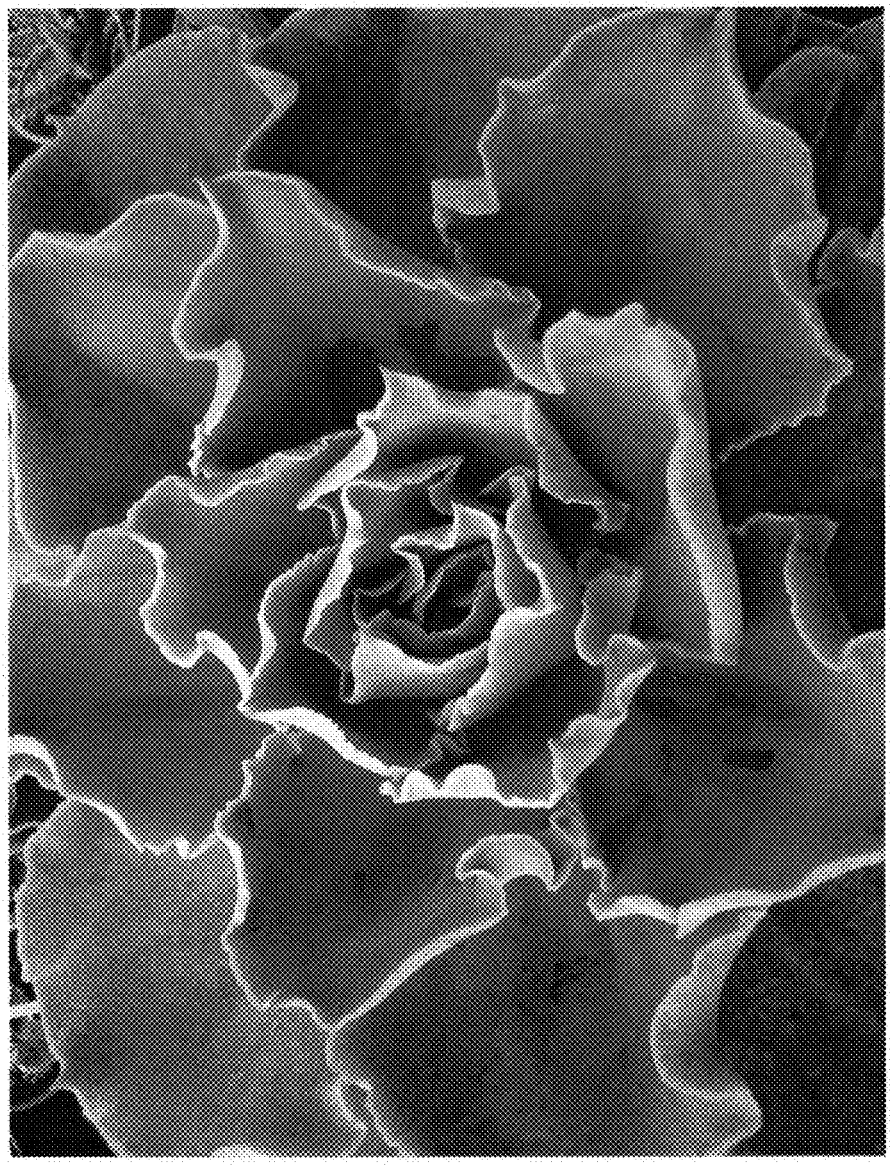
FIG. 1 illustrates in full color the top view of a rosette typical of plants of *Echeveria* 'Andromeda' grown in a greenhouse in Vista, Calif.
Figure 2:
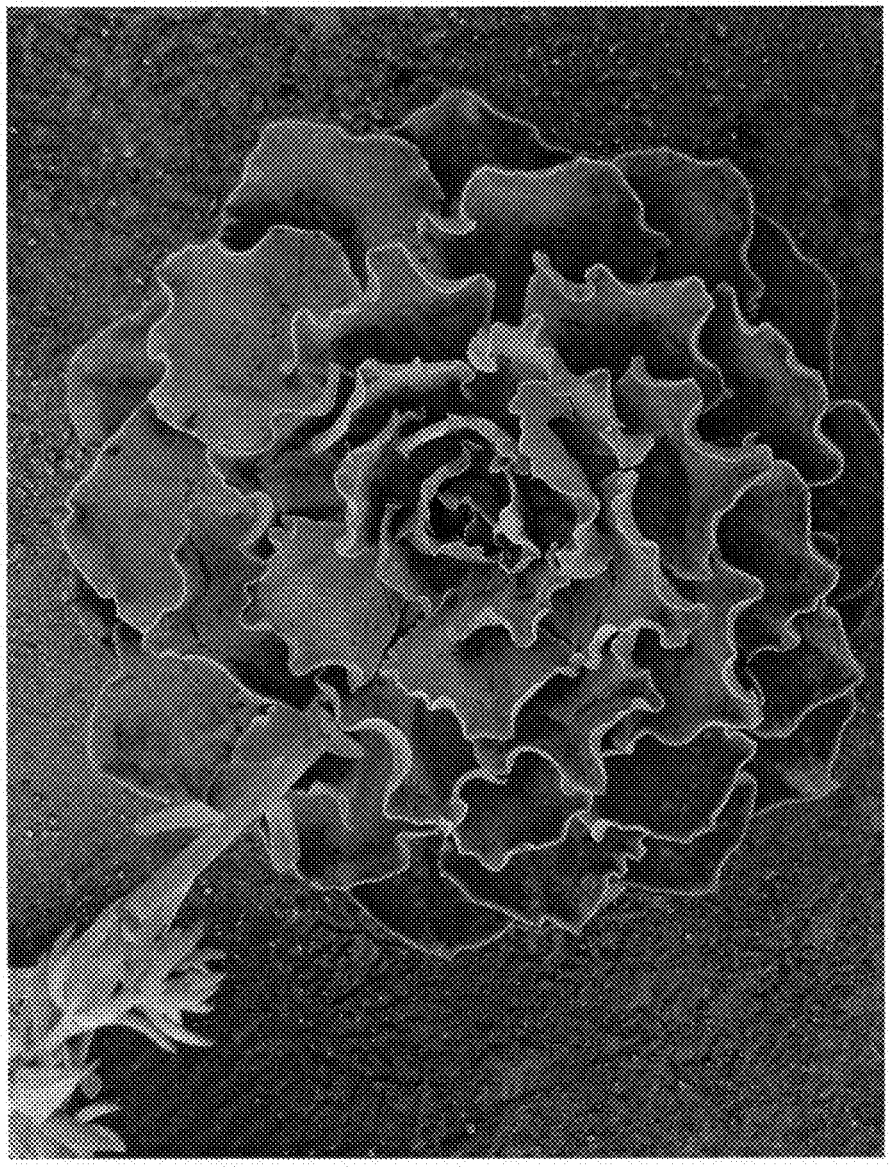
FIG. 2 illustrates in full color the side view of a rosette typical of plants of *Echeveria* 'Andromeda' grown in a commercial greenhouse in Vista, Calif.
Figure 3:
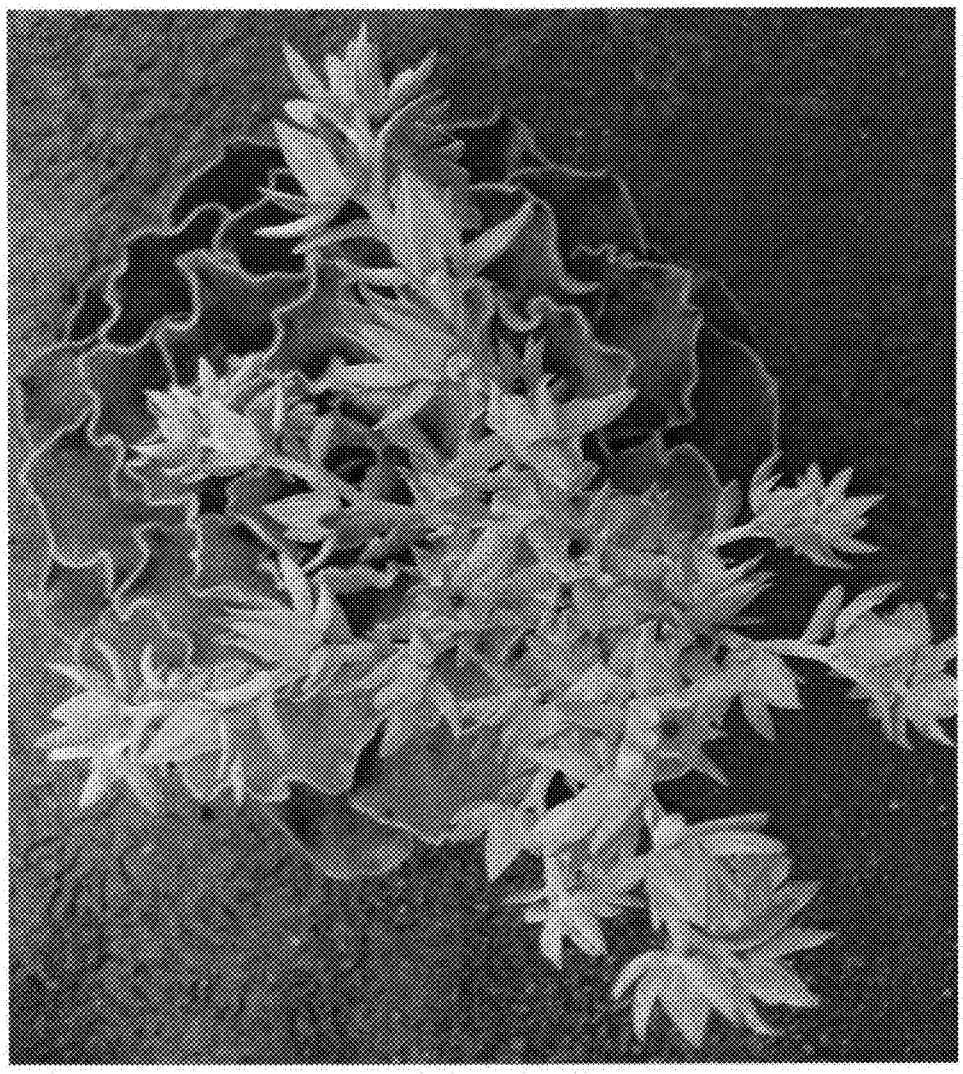
FIG. 3 illustrates in full color a top view of the inflorescence typical of plants of *Echeveria* 'Andromeda' grown in a commercial greenhouse in Vista, Calif.

In the following description, color references are made to the Pantone Process Color System Guide, Pantone CYMK, 2014, except where general terms of ordinary dictionary significance are used. The following observations and measurements describe 'Andromeda' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'ANDROMEDA'.

PROPAGATION

Type of propagation typically used: Terminal vegetative cuttings.

Time to initiate roots: About 14 days at approximately 24° C.

Root description: Fibrous.

PLANT

Age of plant described: Approximately 4 months.

Container size of the plant described: 19.5 cm.

Growth habit: Densely rosette plant.

Height: Approximately 19.5 cm to top of highest leaf. Approximately 71.0 cm. to top of highest inflorescence.

Plant spread: Approximately 36 cm.

Growth rate: Moderately fast.

Branching characteristics: Infrequently until approximately 12 inches in diameter. At this size, plants begin to produce offsets.

FOLIAGE

Leaf:

*Arrangement.*—Rosulate.

*Average length.*—Approximately 14 cm. Longest 21 cm.

*Average width.*—8.0 cm.

*Widest width.*—Approximately 12 cm.

*Width at base.*—2.6 cm.

*Shape of blade.*—Obovate.

*Apex.*—Acute, mucronate.

*Base.*—Elliptical.

*Margin.*—Slightly undulate crispate.

*Texture of top surface.*—Glabrous, glaucous.

*Texture of bottom surface.*—Glabrous, glaucous.

*Quantity of leaves per plant.*—Approximately 57.

*Color.*—Young foliage upper side, middle of leaf: Near S 326-6 Pantone. Some areas of S 327-5 Pantone. Young foliage, upper side, margin near apex: Near S 142-4 Pantone. Young foliage, upper side, margin mid leaf: Near S 148-8 Pantone. Young foliage, under side: Near S 327-7 Pantone; if glaucous layer is removed, near S 329-4 Pantone. Young foliage, under side: Near S 327-7 Pantone; if glaucous layer removed, near S 329-4 Pantone. Mature foliage, upper side: Near S 281-8 Pantone; near S 298-6 Pantone, where glaucous coating has been removed. Mature foliage upper side, mid leaf: Near S 325-5 Pantone. Mature foliage, apical margin: Near S 121-2 Pantone to S 121-1 Pantone. Mature foliage, under side: Near S 159-15 Pantone & S 159-6 Pantone. Mature foliage, under side, apical margin: Near S 166-3 Pantone. Mature foliage, under side, near stem: Near S 160-11 Pantone.

*Venation*.—There is no visual appearance of venation.

FLOWER

Natural flowering season: May and June.

Inflorescence type and habit: Erect inflorescence composed of 3-5 cincinii of 17-20 flowers each.

Rate of flower opening: 1 flower opens every 2-3 days.

Flower longevity on plant: 3-4 days, depending upon ambient temperatures.

Quantity of flowers: 68.

*Total inflorescence size*.—Height: Approximately 48 cm. Width: Approximately 18 cm.

*Corolla*.—Arrangement: Pentagonal. Size: Length: Approximately 2.4 cm. Width: Approximately 1.5 cm at widest point. Lobe Length: Approximately 2.2 cm. Lobe width: Approximately 0.7 cm. Petal Texture: Interior and exterior surfaces glabrous.

Petals:

*Color*.—When opening: Petal color, outer surface: Near S 156-6 Pantone. Petal color, outer surface, near apex: Near S 151-4 Pantone. Petal color, inner surface: Near S 90-3 Pantone. Petal color, inner apex: Near S 98-1 Pantone. Fully opened: Outer surface: Near S 129-5 Pantone. Inner surface, near base: Near S 90-4 Pantone. Inner surface, near apex: Near S 90-2 Pantone. Color Changes when Aging: Near S 138-3 Pantone.

Bud: (near opening).

*Shape*.—Conical.

*Length*.—Approximately 1.8 cm.

*Diameter*.—Approximately 1.2 cm.

*Color*.—Near S 129-5. Apex near S 172-4 Pantone.

Sepals:

*Margin*.—Entire.

*Shape*.—Deltoid.

*Apex*.—Acute.

*Texture*.—Glabrous.

*Color*.—Outer corolla: Near S 187-7 Pantone. Inner corolla: Near S 195-7 Pantone.

*Length*.—Approximately 8 mm.

*Width*.—Approximately 4 mm.

Pedicels:

*Length*.—Approximately 0.9 cm.

*Width*.—Approximately 0.2 cm.

*Strength*.—Strong, flexible.

*Texture*.—Glabrous.

*Color*.—Near S 49-7 Pantone.

*Fragrance*.—None detected.

REPRODUCTIVE ORGANS

Stamens: (Androecium).

*Number*.—Average 10.

*Filament length*.—Approximately 1.1 cm.

*Filament color*.—Near S 32-6 Pantone.

*Anther length*.—2.0 cm.

*Anther color*.—Near S 321-4 Pantone.

*Anther shape*.—Oblong.

*Pollen color*.—Near S 18-5 Pantone.

*Pollen quantity*.—Moderate.

Pistil: (Gynoecium).

*Number*.—Average 5.

*Length*.—Approximately 1.3 cm.

*Style color*.—Near S 137-8 Pantone.

*Stigma*.—Shape: Globose. Color: Near S 317-8 Pantone. Ovary Color: Near S 148-7 Pantone, blending to S 148-4 Pantone nearing style.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: Neither resistance or susceptibility to normal diseases and pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'ANDROMEDA' as herein illustrated and described.

* * * * *